(12) United States Patent
Low

(10) Patent No.: US 9,364,163 B2
(45) Date of Patent: Jun. 14, 2016

(54) CORRELATING BRAIN SIGNAL TO INTENTIONAL AND UNINTENTIONAL CHANGES IN BRAIN STATE

(71) Applicant: NeuroVigil, Inc., La Jolla, CA (US)

(72) Inventor: Philip Steven Low, La Jolla, CA (US)

(73) Assignee: NeuroVigil, Inc., La Jolla, CA (US)

( * ) Notice: Subject to any disclaimer, the term of this patent is extended or adjusted under 35 U.S.C. 154(b) by 283 days.

(21) Appl. No.: 13/749,619

(22) Filed: Jan. 24, 2013

(65) Prior Publication Data

US 2014/0031711 A1    Jan. 30, 2014

Related U.S. Application Data

(60) Provisional application No. 61/590,235, filed on Jan. 24, 2012.

(51) Int. Cl.
| | |
|---|---|
| *A61B 5/048* | (2006.01) |
| *A61B 5/16* | (2006.01) |
| *A61B 5/00* | (2006.01) |
| *A61B 5/0476* | (2006.01) |
| *A61B 5/0488* | (2006.01) |
| *A61B 5/0496* | (2006.01) |

(52) U.S. Cl.
CPC . *A61B 5/048* (2013.01); *A61B 5/16* (2013.01); *A61B 5/4076* (2013.01); *A61B 5/0476* (2013.01); *A61B 5/0488* (2013.01); *A61B 5/0496* (2013.01); *A61B 5/4094* (2013.01)

(58) Field of Classification Search
CPC ...... A61B 5/0476; A61B 5/16; A61B 5/7264; A61B 5/0482; A61B 5/04842; A61B 5/4094; A61B 5/048; A61B 5/0488; A61B 5/0496; G06F 3/015; G06F 19/36; G06K 9/00563
See application file for complete search history.

(56) References Cited

U.S. PATENT DOCUMENTS

| | | |
|---|---|---|
| 5,083,571 A | 1/1992 | Prichep |
| 5,154,180 A | 10/1992 | Blanchet et al. |
| 6,731,975 B1 | 5/2004 | Viertio-Oja et al. |
| 6,993,380 B1 | 1/2006 | Modarres |

(Continued)

FOREIGN PATENT DOCUMENTS

| | | |
|---|---|---|
| AU | 2009313766 A1 | 7/2011 |
| CA | 2779265 A1 | 5/2010 |

(Continued)

OTHER PUBLICATIONS

Peter Anderer, et al.; An E-Health Solution for Automatic Sleep Classification according to Rechtschaffen and Kales: Validation Study of the Somnolyzer 24×7 Utilizing the Siesta Database; Neuropsychobiology 2005, pp. 115-133, vol. 51, published online: Apr. 18, 2005, www.karger.com/nps, © 2005 S. Karger AG, Basel.

(Continued)

*Primary Examiner* — Christine H Matthews
*Assistant Examiner* — Joshua D Lannu
(74) *Attorney, Agent, or Firm* — DLA Piper LLP (US)

(57) ABSTRACT

Methods of analysis to extract and assess brain data collected from subject animals, including humans, to detect intentional and unintentional brain activity and other unexpected signals are disclosed. These signals are correlated to higher cognitive brain functions or unintended, potentially adverse events, such as a stroke or seizure, and to translation of those signals into defined trigger events or tasks.

26 Claims, 10 Drawing Sheets

(56) References Cited

U.S. PATENT DOCUMENTS

| | | | |
|---|---|---|---|
| 8,073,534 | B2 | 12/2011 | Low |
| 2002/0082513 | A1 | 6/2002 | Ennen et al. |
| 2003/0032893 | A1 | 2/2003 | Koch |
| 2003/0153841 | A1 | 8/2003 | Kilborn |
| 2004/0010203 | A1 | 1/2004 | Bibian et al. |
| 2007/0016095 | A1* | 1/2007 | Low et al. .............. 600/544 |
| 2007/0105180 | A1 | 5/2007 | Shaw |
| 2008/0071326 | A1 | 3/2008 | Heruth |
| 2009/0048506 | A1 | 2/2009 | Fong-Ichimura et al. |
| 2009/0156956 | A1* | 6/2009 | Milgramm et al. .......... 600/544 |
| 2009/0253996 | A1 | 10/2009 | Lee |
| 2010/0016752 | A1* | 1/2010 | Sieracki .............. 600/544 |
| 2010/0168603 | A1* | 7/2010 | Himes et al. ............ 600/544 |
| 2011/0098593 | A1 | 4/2011 | Low |
| 2011/0218454 | A1 | 9/2011 | Low |
| 2012/0029378 | A1 | 2/2012 | Low |

FOREIGN PATENT DOCUMENTS

| | | | |
|---|---|---|---|
| CN | 102438515 | A | 5/2012 |
| EP | 1885237 | A2 | 2/2008 |
| EP | 2355700 | A2 | 8/2011 |
| EP | 2493377 | A | 9/2012 |
| JP | 2012508628 | A | 4/2012 |
| KR | 2003-0002677 | A | 1/2003 |
| KR | 2008-0025673 | A | 5/2005 |
| KR | 2007-0109044 | A | 10/2007 |
| KR | 2011-0094064 | A | 8/2011 |
| WO | WO2006-122201 | A3 | 11/2006 |
| WO | WO2006121455 | A1 | 11/2006 |
| WO | WO2010057119 | A2 | 5/2010 |
| WO | WO2011-056679 | A2 | 5/2011 |

OTHER PUBLICATIONS

Alejandro Chediak, et al.;How Many Polysomnograms Must Sleep Fellows Score Before Becoming Proficient at Scoring Sleep?; Mar. 15, 2006, pp. 427-430, Journal of Clinical Sleep Medicine, vol. 2, No. 4 2006, Miami Sleep Disorders Center, Miami, FL.

Heidi Danker-Hopfe, et al.; Interrater reliability between scorers from eight European sleep laboratories in subjects with different sleep disorders; Sep. 13, 2003, pp. 63-69, J Sleep Res. 13, © 2004 European Sleep Research Society.

Alain Destexhe, et al.;Spatiotemporal Analysis of Local Field Potentials and Unit Discharges in Cat Cerebral Cortex during Natural Wake and Sleep States; Jun. 1, 1999, pp. 4595-4608, The Journal of Neuroscience, © 1999 Society for Neuroscience.

Alain Destexhe and Terrence J. Sejnowski;Thalamocortical Assemblies; 2001, pp. 347-391,Monographs of the Physiological Society 49, www.oup.com, Oxford Univ. Press, Oxford.

Arthur Flexer, et al.; A reliable probabilistic sleep stager based on a single EEG signal; Apr. 8, 2004, pp. 1-26, Austrian Research Institute for Artificial Intelligence, Vienna AU and UCSD La Jolla, CA USA.

Damien Gervasoni, et al.;Global Forebrain Dynamics Predict Rat Behavioral States and Their Transitions; Dec. 8, 2004, pp. 11137-11147, J. Neurosci. 24, © 2004 Society for Neuroscience.

Claude Gottesmann, The Transition from Slow-wave Sleep to Paradoxical Sleep: Evolving Facts and Concepts of the Neurophysiological Processes Underlying the Intermediate Stage of Sleep; 1996, pp. 367-387, vol. 20, No. 3 Neuroscience and Biobehavioral Reviews, © 1996 Elsevier Science Ltd. Printed in Great Britain.

Sari-Leena Himamen and Joel Hasan;Limitations of Rechtschaffen and Kales; J., 2000, pp. 149-167, vol. 4, No. 2, Sleep Medicine Reviews, http://www.idea © 2000 Harcourt Publishers Ltd.

James T. Kelley, et al.; Reliability of Rapid Clinical Staging of Sleep EEG; 1985, pp. 16-20, vol. 16 No. 1, Clinical Electroencephalography, © 1985.

Rodolfo Llinas and Urs Ribary,Coherent 40-Hz oscillation characterizes dream state in humans; Mar. 1993, pp. 2078-2081,Neurobiology, Proc. Natl. Acad. Sci. USA.

S. Roberts and L. Tarassenko; Analysis of the sleep EEG using a multilayer network with spatial organisation; Dec. 1992, pp. 420-425, vol. 139, No. 6, IEE Proceedings—F 992.

PCT Notification of Transmittal of Search Report and the Written Opinion of the International Searching Authority for PCT/US2013/023033 dated Jun. 25, 2013 and its entire file history, related to present application Examiner has access to file history, to notify Applicants' attorney if documents need to be submitted.

* cited by examiner

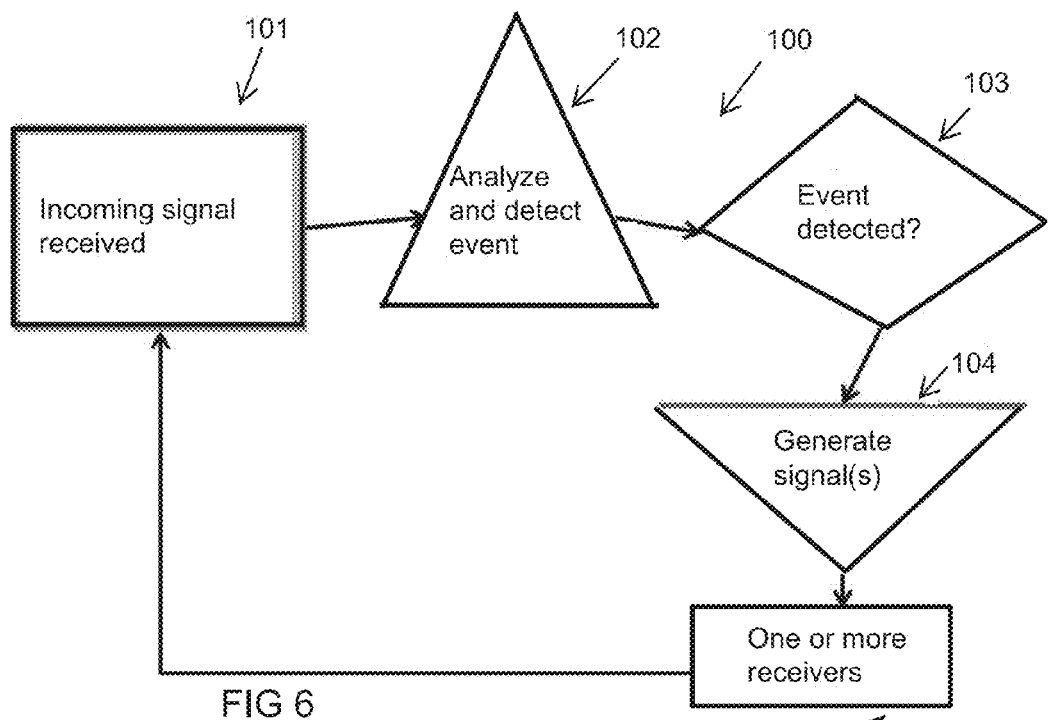
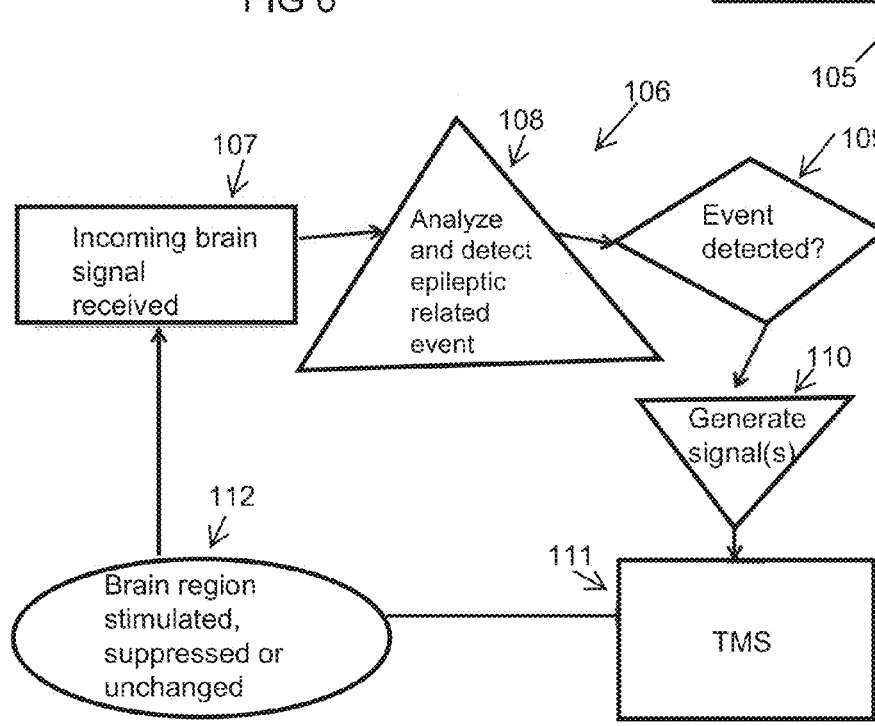
FIG 7

CORRELATING BRAIN SIGNAL TO INTENTIONAL AND UNINTENTIONAL CHANGES IN BRAIN STATE

CROSS REFERENCE

This application claims priority from U.S. Provisional Patent Application Ser. No. 61/590,235 filed Jan. 24, 2012 incorporated herein in its entirety by reference.

FIELD OF INVENTION

This invention is directed to methods of analysis to extract and assess brain data collected from subject animals, including humans, to detect intentional brain signals and unintentional and other unexpected brain signals. These signals are correlated to higher cognitive brain functions or unintended, potentially adverse events, such as a stroke or seizure, and to translation of those signals into defined trigger events or tasks. More particularly the present invention is directed to a physiological data acquisition from EEG, EMG, EOG, MEG, ECoG, iEEG, fMRI, LFP or other signals obtained from a peripheral channel modulated by the subject's brain activity or modulating brain activity.

BACKGROUND OF THE INVENTION

An Electroencephalogram (EEG) is a tool used to measure electrical activity produced by the brain. The functional activity of the brain is collected by electrodes placed on the scalp. The EEG has traditionally supplied important information about the brain function of a patient. Scalp EEG is thought to measure the aggregate of currents present post-synapse in the extracellular space resulting from the flow of ions out of or into dendrites that have been bound by neurotransmitters. Accordingly, EEG and like modalities are mainly used in neurology as a diagnostic tool for epilepsy but the technique can be used in the study of other pathologies, including sleep disorders.

Recent advances in EEG and other signal detection have allowed for the automated, real time, detection of sleeping and waking states through the normalization and other manipulation of brain activity data. In addition, such applications and methods can also be used to automatically access pathological conditions and medication effects. Related technology has allowed for the accessing of such data in real time utilizing a single channel detector. This in turn has provided the opportunity to further dissect sleep and waking states, including clear differentiation between REM and deep sleep states. To aid in the efficient collections of such data, head and harness systems have been developed utilizing single channels and wireless data transmission. See, e.g., International Patent Application Number PCT/US2006/018120; International Patent Application Number PCT/US2009/064632; International Patent Application Number PCT/US2010/054346; U.S. Pat. No. 8,073,574; and Low, Philip Steven (2007). "A new way to look at sleep: separation and convergence". Published Thesis, University of California San Diego Electronic Theses and Dissertations (Identified: b6635681), the disclosures of which are herein incorporated by reference in their entirety. To date, this technology has been primarily applied to sleep-related diagnostic applications, and the impact of pathologies and medications.

Development has continued in the area of exoskeletons and related prostheses that hold the promise to allow paraplegics to walk again and perform other tasks that they currently are unable to perform. In addition, such devices may also be useful with healthy individuals, such as soldiers in the field, first responders, construction works etc. Companies such as Esko Bionics, Parker Hannifan and Argo Medical Technologies and consistently advancing such technologies. See, e.g., U.S. Pat. No. 8,096,965; International Patent Application Number WO2010101595A1, and U.S. patent application Ser. No. 11/600,291, filed Nov. 15, 2006. In addition, other devices are utilized to allow severely compromised individuals with ALS, MS and the like to communicate using voice synthesizers and the like. Typically, such devices are activated by movement of a cheek muscle, eye using Eye Tracker or the like.

There is therefore a need for non-invasive methods to detect the intentional and unintentional communication from subjects, including disabled individuals, to assess and potentially respond to or prepare for the physiological implications of these changes in brain state.

SUMMARY OF THE INVENTION

The present invention provides methods to non-invasively detect the intentional and unintentional communication from healthy and diseased subjects, including disabled individuals with neurological diseases such as ALS, MS and the like, in the form of physiological data through, e.g. EEG, EMG, EOG, MEG, ECoG, iEEG, fMRI, LFP and the like and to correlate these intentional and unintentional signals to changes in brain state, including higher cognitive functions. There is also a need to utilize such intentional communication to, e.g., simulate speech or move an artificial prosthesis. There is further a need to access unintentional signals from a subject with a pathological condition, such as epilepsy (or diseases in the body causing changes in brain activity), to be correlated with a pathological condition and to optionally be used to trigger an alarm and/or to intervene to alter, suppress or prepare for an unintended event.

In a preferred method of the present invention, intentional brain signals from a subject are detected by attaching at least a single sensor to the subject, obtaining data indicative of brain activity, analyzing said data indicative of brain activity; and correlating said analyzed data to an intentional higher cognitive function from the subject. Preferably, the data is obtained non-invasively by applying at least the single sensor to the subject, and more preferably by applying at least a single dry sensor or at least a single wet sensor. Further, it is preferred that the data is received from at least a single channel of EEG, EMG, EOG, MEG, ECoG, iEEG, fMRI, LFP or a peripheral channel modulated by the subject's intention. In an alternative embodiment, the data is received through a multi channel detector. Further, it is preferred that the data is communicated and received wirelessly.

In another preferred embodiment, the data is analyzed by normalizing a spectrogram, including a normalized spectrogram, of the data at least once, time over frequency, and normalizing the spectrogram, including a normalized spectrogram, of the same data at least once, frequency over time, where both normalizations can be performed in either order and can be iterated. In a further preferred embodiment, the data is analyzed by computing the spectrogram of the data, normalizing the spectrogram, performing an independent or principal component analysis of the normalized spectrogram, and identifying clusters. In addition, the analyzing step can also include performing a temporal fragmentation analysis, preferred frequency analysis, an iterated (preferably two times or more) preferred frequency analysis, and/or spectral fragmentation analysis.

In an especially preferred embodiment, the methods of the present invention further comprise translating the analyzed data to effect a task associated with the higher cognitive function, including, but not limited to, intent, speech, memory recall, thought, imagination and planning, including but not limited to motion. Importantly, the task effected by translating the analyzed data includes simulating speech on a display, simulating speech with a voice synthesizer, or movement of an artificial prosthesis, or movement of an exoskeleton and the like.

In yet another preferred embodiment of the methods of the present invention, brain signals from a subject are correlated with at least one unintended event by attaching at least a single sensor to the subject, obtaining data indicative of brainwave activity, analyzing said data indicative of brain activity, and correlating said analyzed data to at least one unintended event. In a further embodiment, after correlating the data to an unintended event, an alarm is triggered. Alternatively, after correlating the data to an unintended event, a response can be triggered to ameliorate the effect of the unintended event, which can include altering, suppressing or preparing for the unintended event (which may also trigger an alarm). This response will be especially impactful where the unintended event high fragmentation event, a change in fragmentation of an event, a surprise, a tremor, a spasm, an injury or a pathology including but not limited to, an epileptic seizure, a migraine, a stroke, a heart attack or an infarction.

In another preferred embodiment, the methods of the present invention detect intentional signals from a subject by attaching at least one detector capable of detecting the intentional signal to the subject, obtaining data indicative of detected activity using EEG, EMG, EOG, MEG, ECG, ECoG, iEEG, LFP, fMRI or a peripheral channel modulated by the intentional signals from a subject, analyzing said data indicative of the detected activity, and correlating said analyzed data to an intentional higher cognitive function from the subject. It is contemplated that any method, system or information described herein can be implemented with respect to any other method, system or information described herein.

Unless otherwise defined, all terms used herein have the same meaning as commonly understood by one of ordinary skill in the art to which this invention belongs. Methods and materials are described herein for use of the present invention; other suitable methods and materials known in the art can also be used. The materials and methods, and examples are illustrative only and not intended to be limiting. All publications, patent applications, patents and other references mentioned herein, are incorporated by reference in their entirety. In case of conflict, the present specification, including definitions will control.

These and other embodiments of the invention will be better appreciated and understood when considered in conjunction with the following description and the accompanying drawings. It should be understood, however, that the following description, while indicating various embodiments of the invention and numerous specific details thereof, is given by way of illustration and not of limitation. Many substitutions, modifications, additions and/or rearrangements may be made within the scope of the invention without departing from the spirit thereof, and the invention includes all such substitutions, modifications, additions and/or rearrangements.

BRIEF DESCRIPTION OF THE DRAWINGS

For the present invention to be clearly understood and readily practiced, the present invention will be described in conjunction with the following figures, wherein like reference characters designate the same or similar elements, which figures are incorporated and constitute a part of the specification.

FIG. 6 is a flow chart illustrating the application of the methods of the present invention to intentional signals.

FIG. 7 is a flow chart illustrating the application of the methods of the present invention to unintentional signals in, e.g., epilepsy.

DETAILED DESCRIPTION

Figure 1:
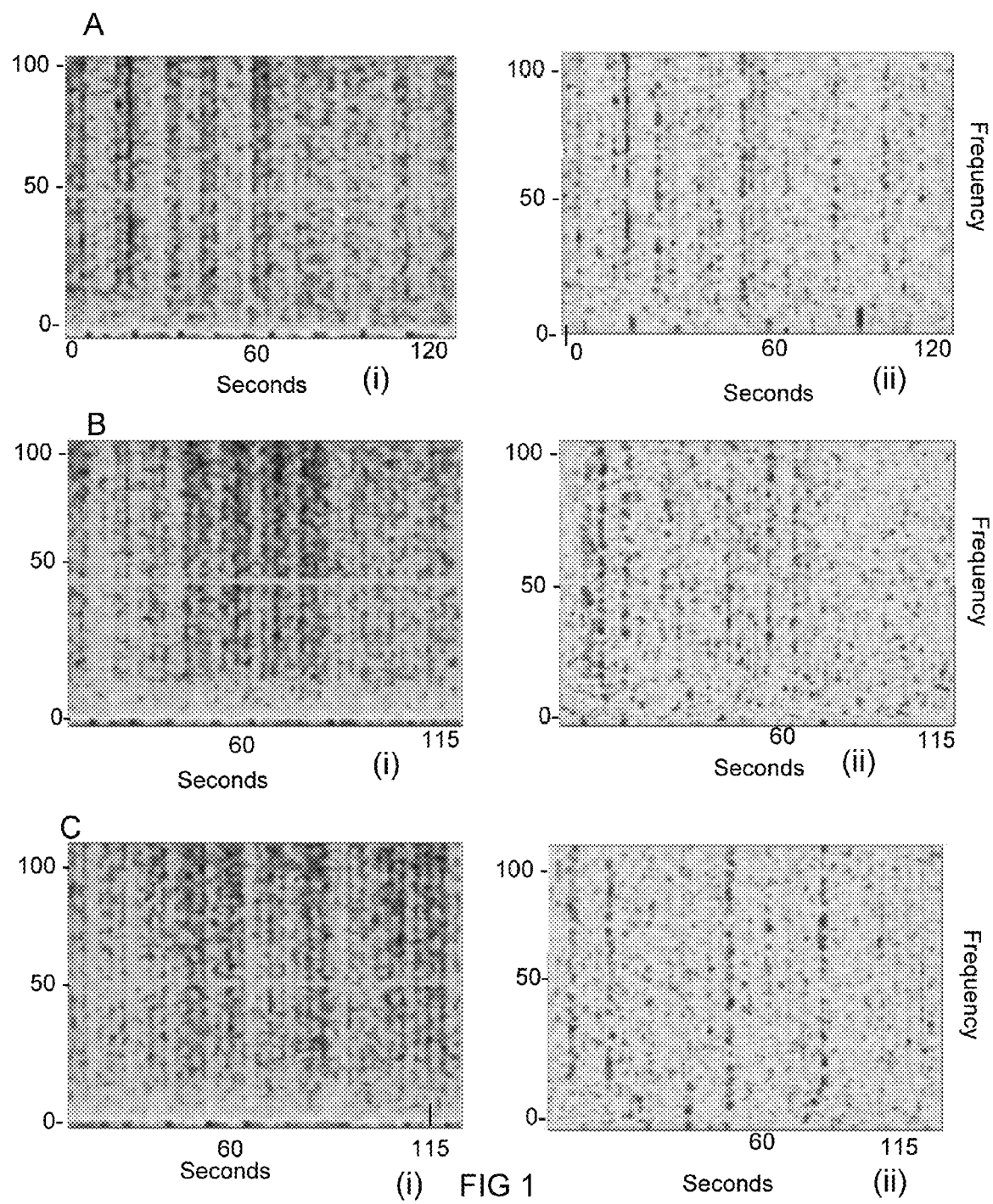
FIG. 1 is a series of graphs illustrating examples of bring signal analyses. The left column shows traditional analyses and the right column shows analyses using the methods of the present invention on closed eyes (A), squeeze left hand (B), squeeze right hand (C), squeeze left foot (D), and squeeze right foot (E). The final two graphs (F) illustrate the traditional analysis in the left column and analyses using the methods of the present invention in the right column on the subject in a resting state.
Figure 1:
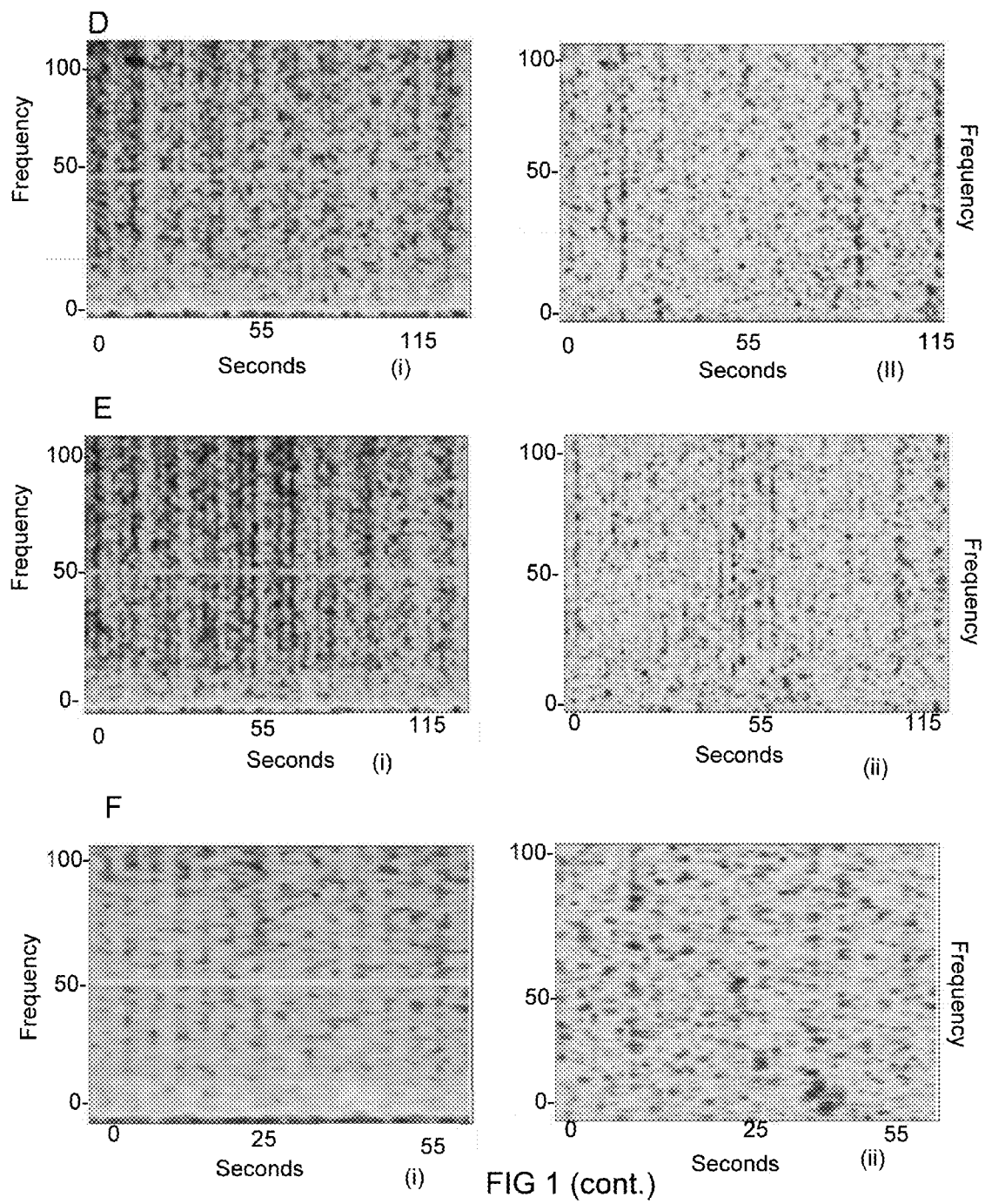

It is to be understood that the figures and descriptions of the present invention have been simplified to illustrate elements that are relevant for a clear understanding of the invention, while eliminating, for purpose of clarity, other elements that may be well known. The detailed description will be provided herein below with reference to the attached drawings.

A detailed description of one or more embodiments of the invention is provided below along with accompanying figures that illustrate the principles of the invention. The invention is described in connection with such embodiments, but the invention is not limited to any embodiment. The scope of the invention is limited only by the claims and the invention encompasses numerous alternatives, modifications and equivalents. Numerous specific details are set forth in the following description in order to provide a thorough understanding of the invention. These details are provided for the purpose of example and the invention may be practiced according to the claims without some or all of these specific details. For the purpose of clarity, technical material that is known in the technical fields related to the invention has not been described in detail so that the invention is not unnecessarily obscured.

The term "subject" in this application refers to both animals and humans.

Referring now to FIG. 6, wherein is disclosed a flow chart 100 illustrating a preferred embodiment of the present methods. Specifically, the subject visualizes and creates an intentional brain signal that is received by at least a single sensor 101 according to the present invention. Preferably, this sensor comprises a single wet electrode or a single dry electrode. The incoming signal is relayed to a computational device, such as a computer, where it is analyzed 102 to determine if a defined event has occurred 103. Preferably, this indicative of brain activity that correlates to a higher cognitive function from the subject. The computer then generates a signal 104 that is relayed to one or more receivers 105 on a peripheral device. Examples of peripheral devices may include voice synthesizers, prosthetic devices, including exoskeletons and the like. As noted in FIG. 6, these methods preferably occur in real time and provide a continuous response and feedback look between the intentional signals of the subject and the translation of those signals into commands associated with the peripheral devices controlled by intentions of the subject. In an especially preferred embodiment, the data signal from the subject is received from at least a single channel of EEG, EMG, EOG, MEG, ECoG, iEEG, fMRI, LFP or a peripheral channel modulated by the subject's intention. In a preferred alternative, the data is received through a multi channel detector that interfaces wirelessly with the computing device and peripheral device(s).

Referring now to FIG. 7, wherein is disclosed another flow chart 106 illustrating an alternative preferred embodiment of the present methods. Specifically, the subject is monitored for presence of unintended events (e.g., a stroke or a seizure) via a brain signal that is received by at least a single sensor 107 according to the present invention. Preferably, this sensor comprises a single wet electrode or a single dry electrode. The incoming signal is relayed to a computational device, such as a computer, where it is analyzed 108 to determine if the defined unintentional event has occurred 109. There are numerous examples of potentially harmful, unintentional events, including, but not limited to, a surprise, a tremor, a spasm, an injury or a pathology including but not limited to, an epileptic seizure, a migraine, a stroke, a heart attack or an infarction.

The computer then generates a signal 110 that is relayed to one or more receivers on a peripheral device. In this instance, the peripheral device is stimulating device 111 used to ameliorate the effect of an impending seizure in and epileptic patient by stimulating the brain region 112 of the subject. As will be appreciated by those skilled in the art, the peripheral device 111 may also suppress or not change (or effect) the subject 112. For example, the triggering of an alarm to alert the subject or a caregiver. In an especially preferred embodiment, the data signal from the subject is received from at least a single channel of EEG, EMG, EOG, MEG, ECoG, iEEG, fMRI, LFP or a peripheral channel modulated by the unintentional occurrence of the unintended event being monitored. In a preferred alternative, the data is received through a multi channel detector that interfaces wirelessly with the computing device and peripheral device(s).

In another preferred embodiment of the methods illustrated in both FIGS. 6 and 7, the data is analyzed by normalizing a spectrogram, including a normalized spectrogram, of the data at least once, time over frequency, and normalizing the spectrogram, including a normalized spectrogram, of the same data at least once, frequency over time, where both normalizations can be performed in either order and can be iterated. In a further preferred embodiment, the data is analyzed by computing the spectrogram of the data, normalizing the spectrogram, performing an independent or principal component analysis of the normalized spectrogram, and identifying clusters. In addition, the analyzing step can also include performing a temporal fragmentation analysis, preferred frequency analysis, an iterated (preferably two times or more) preferred frequency analysis, and/or spectral fragmentation analysis.

In a preferred embodiment, detecting brain signals (e.g., high-frequency signals detected from the brain) and correlating the detected signals to higher cognitive function is disclosed. Examples of higher cognitive functions include, among others, intent, speech, memory recall, thought, imagination, and planning, including but not limited to motion, and directed task involving imagination and other cognitive processes and functions.

In some embodiments, a brain signal of a subject is translated into speech. For example, when the subject imagines one or more elements of language, including but not limited to a letter, number, word or symbol, a brain signal associated with this or multiple elements of language, is detected and this or multiple elements of language is determined. In another example, a subject with impaired speech capability is taught to associate an image, symbol, word, letter or number with an imaginary movement. When the subject imagines the imaginary movement, a brain signal associated with the imaginary movement is detected and the word, letter or number associated with imaginary movement is determined. In an embodiment, the subject's imaginary movement controls a cursor on a display which selects the image, symbol, word, letter or number the subject intends to use. In some embodiments, the determined image, symbol, word, letter or number is used with one or more other determined images, symbols, words, letters or numbers to construct grammatical speech. In some embodiments, the determined image, symbol, word, letter or number is communicated using voice synthesizers and/or displayed. In some embodiments, the brain signal and/or the output is assigned a non-linguistic value including but not limited to a tone, series of tones, micropitch, color, image, electrical stimulation, uni or multidimensional graphic. In some embodiments, the brain signal and/or the output is assigned to a brain signal. In some embodiments, the brain signal follows and/or precedes and/or occurs simultaneously with one or more endogenous and/or exogenous event and/or state including, but not limited to a pathological and/or altered event and/or state.

In some embodiments, a brain signal of a subject is translated to a movement of an artificial prosthesis. For example, a detected brain signal associated with an imaginary movement is used at least in part to control an artificial prosthesis.

In some embodiments, one or more physiological recordings, including but not limited to EEG, EMG, EOG, MEG, ECoG, iEEG, fMRI, LFP, or a peripheral channel modulated by the subject's intention or reading unintentional signals for unintended events is used to detect one or more brain signals. For example, a Single-Channel iBrain EEG recording is conducted on a high-functioning 70 year old ALS patient attempting to move one of four limbs after a verbal cue: the left and right hand and foot. EEG signals are analyzed with algorithms, including the SPEARS algorithm, in order to make brain signals detectable. Concurrent video recordings may be obtained. During the attempted movements, the subject's brain activity demonstrates broad spectrum pulses extending to the Gamma and ultra-high Gamma ranges. Such pulses are present in the absence of actual movement and absent when the subject was not attempting motion. Activity in the Alpha range is detected when the subject closed his eyes. Such high bandwidth biomarkers opens the possibility to link intended movements to a library of words and convert them into speech, providing ALS sufferers with communication tools utilizing brain signals.

In some embodiments, clear broad spectrum patterns of activation across many frequencies can be detected for actual or imaginary movements as compared to different patterns for the resting state. These patterns match the timing of a subject's actual or imaginary movements. Traditional spectral analysis does not reveal such patterns. Analytics on physiological data may be used to detect brain signals that correlate in time with a subject's actual or imaginary movements. In some embodiments, these signals are transmitted and parsed in real time to provide additional degrees of freedom for brain based communication.

The methods described herein are disclosed in detail in International Patent Application Number PCT/US2006/018120; International Patent Application Number PCT/US2009/064632; International Patent Application Number PCT/US2010/054346; U.S. Pat. No. 8,073,574; and Low, Philip Steven (2007). "A new way to look at sleep: separation and convergence". Published Thesis, University of California San Diego Electronic Theses and Dissertations (Identified: b6635681), the disclosures of which are herein incorporated by reference in their entirety.

The present invention utilizes a system and method to obtain and classify EEG data in both animals and humans. Obtained EEG signals are low-power frequency signals and follow a 1/f distribution, whereby the power in the signal is inversely related, e.g., inversely proportional, to the frequency.

EEG signals have typically been examined in time in series increments called epochs. The epochs can be segmented into different sections using a scanning window, where the scanning window defines different sections of the time series increment. The scanning window can move via a sliding window, where sections of the sliding window have overlapping time series sequences. An epoch can alternatively span an entire time series, for example.

In a preferred embodiment of this invention a single channel of EEG was sufficient to obtain the data indicative of intentional (or unintentional or other unexpected) brain activity.

Typically, the source data obtained with the methods of the present invention is adjusted to increase the dynamic range for power within at least one low power frequency range of the frequency spectrum of the source data as compared to a second higher power frequency range. A number of adjustment techniques described herein, including normalization and frequency weighting can be used.

In an embodiment, electroencephalography source data is normalized to increase the low power, higher frequency range data relative to the higher power, lower frequency range data or, more generally, to normalize the powers of the different signal parts.

After the source data is adjusted, various other processing can be done. For example, a visualization of the adjusted source data can be presented. Further, low power frequency information can be extracted from the adjusted source data. For example, low power frequency information can be extracted from adjusted electroencephalography source data. Higher power frequency information can also be extracted from the adjusted source data.

Figure 9:
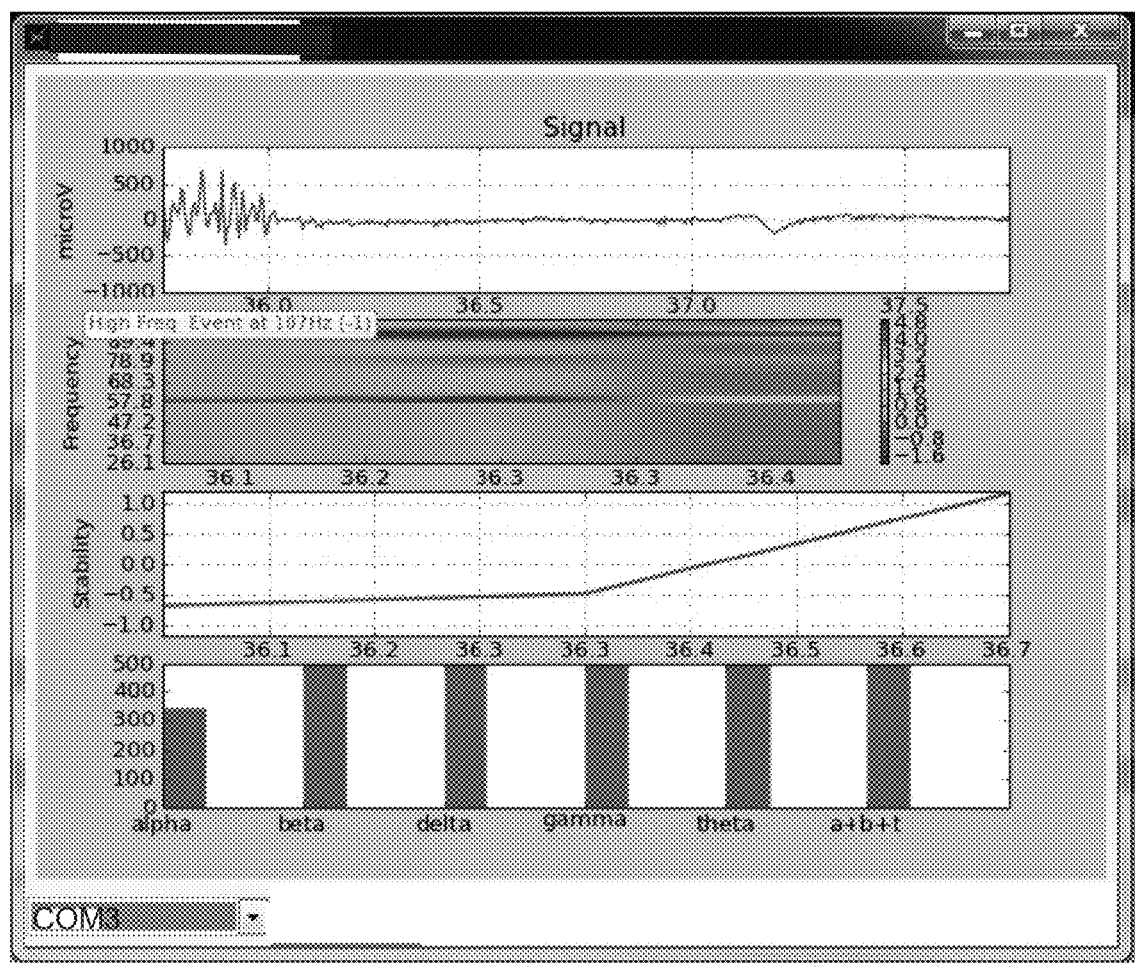
FIG. 9 is a screen shot of computer interface using the methods of the present invention.

The method described in this or any of the other examples can be a computer-implemented method performed via computer-executable instructions in one or more computer-readable media. Any of the actions shown can be performed by software incorporated within a signal processing system or any other signal data analyzer system. For example, The invention can be implemented in numerous ways, including as a process; an apparatus; a system; a composition of matter; a computer program product embodied on a computer readable storage medium; and/or a processor, such as a processor configured to execute instructions stored on and/or provided by a memory coupled to the processor. In this regard, FIG. 9 is a screen shot of a computer interface utilizing the methods and outputs of the present invention. In this specification, these implementations, or any other form that the invention may take, may be referred to as techniques. In general, the order of the steps of disclosed processes may be altered within the scope of the invention. Unless stated otherwise, a component such as a processor or a memory described as being configured to perform a task may be implemented as a general component that is temporarily configured to perform the task at a given time or a specific component that is manufactured to perform the task. As used herein, the term 'processor' refers to one or more devices, circuits, and/or processing cores configured to process data, such as computer program instructions.

Another embodiment uses multiple normalizations for even further dynamic range increase. Normalizations can be performed by normalizing frequency across time or time across frequency.

For example, electroencephalography data with at least one low power frequency range can be received. Artifacts in the data can be removed from the source data. For example, artifact data can be manually removed from the source data or automatically filtered out of source data via a filtering (e.g., DC filtering) or data smoothing technique. The source data can also be pretreated with component analysis (e.g., principle or independent component analysis). The source data is segmented into one or more epochs; where each epoch is a portion of data from the series. For example, the source data can be segmented into a plurality of time segments via a variety of separating techniques. Scanning windows and sliding windows can be used to separate the source data into time series increments. The one or more epochs are normalized for differences in power of the one or more epochs across time. For example, the power of each epoch at one or more frequencies can be normalized across time to determine appropriate frequency windows for extracting information. Such normalization can reveal low power, statistically significant shifts in power at one or more frequencies (e.g., Delta, Gamma, Alpha and the like). Any frequency range can be revealed and utilized for analysis. Information can be calculated for each of the one or more epochs after appropriate frequency windows have been established. Such information can include low frequency power (e.g., Delta power), high frequency power (e.g., Gamma power), standard deviation, maximum amplitude (e.g., maximum of the absolute value of peaks) and the sort. Further calculations can be done on the information calculated for each of the one or more epochs creating information such as Gamma power/Delta power, time derivative of Delta, time derivative of Gamma power/Delta power and the like. Time derivatives can be computed over preceding and successive epochs. After calculating the information, that information can then be normalized across the one or more epochs. A variety of data normalization techniques can be conducted including z-scoring and other similar techniques.

Results of the adjustment of source data to account for differences in power over a spectrum of frequencies over time can be presented as one or more epochs of data. For example, frequency weighted epochs can be presented as adjusted source data.

Electroencephalography data for a subject is obtained and input to segment the data into one or more epochs. In practice, epochs are of similar (e.g., the same) length. Epoch length can be adjusted via a configurable parameter. The one or more epochs, in turn, are input to normalize frequency data in the one or more epochs across time, thereby frequency weighting the one or more epochs of electroencephalography data. The one or more frequency weighted epochs are then input into classifier to classify the data into states of intention versus relaxation or non-intention.

For Example, electroencephalography (EEG) data for a subject is received. For example, electroencephalography data, which exhibits lower dynamic range for power in at least one low power first frequency range in a frequency spectrum as compared to a second frequency range in the frequency spectrum, can be received. The electroencephalography data for the subject is segmented into one or more epochs. For example, the EEG data can be segmented into one or more epochs via a variety of separating techniques. Scanning windows and sliding windows can be used to separate the EEG data into one or more epochs. The source data can also be filtered via direct current activity during, prior to, or after segmenting. The source data can also be pretreated with component analysis (e.g., principle or independent component analysis). In entire night EEG data the higher frequencies (e.g., Gamma) exhibit lower power than the lower frequencies (e.g., Alpha, Delta, Theta and the like) in the whole night EEG data. Frequency power of the one or more epochs is weighted across time. For example, the power of each epoch at one or more frequencies can be normalized across time to determine appropriate frequency windows for extracting information. Such normalization can reveal low power, statistically significant shifts in power at one or more frequencies (e.g., Alpha, Delta, Gamma, and the like). Additionally, each epoch can be represented by the frequency with the highest relative power over time to determine appropriate frequency windows for extracting information. Alternatively, component analysis (e.g., principle component analysis (PCA) or independent component analysis (ICA)) can be utilized after normalization to further determine appropriate frequency windows for extracting information. Any frequency range can be revealed and utilized for analysis.

Information can be calculated for each of the one or more epochs after appropriate frequency windows have been established (e.g., after weighting frequency). Such information can include low frequency power (e.g., Alpha power), high frequency power (e.g., Gamma power), standard deviation, maximum amplitude (e.g., maximum of the absolute value of peaks) and the sort. Further calculations can be done on the information calculated for each of the one or more epochs creating information such as Gamma power/Alpha power, time derivative of Delta, time derivative of Gamma power/Alpha power and the like. Time derivatives can be computed over preceding and successive epochs. After calculating the information, it can then be normalized across the one or more epochs. A variety of data normalization techniques can be conducted including z-scoring and the like. The higher frequency data is now more clearly visible.

Intention states in the subject are classified based on the one or more frequency weighted epochs. For example, the one or more frequency weighted epochs can be clustered by any variety of clustering techniques including k-means clustering. The clustering can be done on information calculated from the epochs (e.g., Alpha power, Gamma power, standard deviation, maximum amplitude (Gamma/Alpha), time derivative of Delta, time derivative-of (Gamma/Alpha, and the sort). Component analysis (e.g., PCA or ICA) can be used to determine the parameter space (e.g., types of information used) in the clustering.

Subsequent to clustering, intention state designations can be assigned to the epochs. Intention state designated epochs can then be presented as representations of intention and relaxation (non-intention) states in the subject for the period of time represented by the epoch. Classification can also incorporate manually determined intention states (e.g., manually determined "intended activity" versus "relaxation" states). Additionally, artifact information can be utilized in the classification.

Artifact data can also be used in intention state classification. For example, artifacts can be used to analyze whether epochs initially assigned a intention state designation should be reassigned a new intention state designation due to neighboring artifact data. In such ways, for example, artifact data can be utilized in a data smoothing technique.

Any variety of data smoothing techniques can be used during the assigning of intention states. For example, numbers (e.g., 0 and 1) can be used to represent designated intention states. Neighboring epochs' brain state designation numbers can then be averaged to determine if one of the epochs is inaccurately assigned a intention state designation. Therefore, should a group of epochs be assigned intention state designations representing abrupt jumps in brain states, smoothing techniques can be applied to improve the accuracy of the assigning.

Previous embodiments have shown how normalization, for example using Z scoring, allowed analysis of more information from the brain activity signal. The analysis which was previously carried out normalized power information across frequencies. The normalization preferably used Z scoring, but any other kind of data normalization can be used. The normalization which is used is preferably unitless, like Z scoring. As well-known in the art, z scoring can be used to normalize a distribution without changing a shape of the envelope of the distribution. The z scores are essentially changed to units of standard deviation. Each z score normalized unit reflects the amount of power in the signal, relative to the average of the signal. The scores are converted into mean deviation form, by subtracting the mean from each score. The scores are then normalized relative to standard deviation. All of the z scored normalized units have standard deviations that are equal to unity.

While the above describes normalization using Z scores, it should be understood that other normalizations can also be carried out, including T scoring, and others. Multiple normalizations may also be employed. Normalizations can be performed by normalizing frequency across time or time across frequency.

The above embodiments describe normalizing the power at every frequency within a specified range. The range may be from 0, to 100 hz, or to 128 hz, or to 500 hz. The range of frequencies is only restricted by the sampling rate. With an exemplary sampling rate of 30 KHz, an analysis up to 15 KHz can be done.

According to the present embodiment, additional normalizations are carried out which normalizes the power across time for each frequency. This results in information which has been normalized across frequencies and across time being used to create a normalized spectrogram. This embodiment can obtain additional information from brainwave data, and the embodiment describes automatically detecting different periods of intention and relaxation from the analyzed data. According to an important feature, a single channel of brainwave activity (that is obtained from a single location on the human skull) is used for the analysis. As described above, the obtained data can be one channel of EEG information from a human or other subject. The EEG data as obtained can be collected, for example, using a 256 Hz sampling rate, or can be sampled at a higher rate. The data is divided into epochs, for example 30 second epochs, and characterized according to frequency.

A first frequency normalization is carried out. The power information is normalized using a z scoring technique on each frequency bin. In the embodiment, the bins may extend from one to 100 Hz and 30 bins per hertz. The normalization occurs across time. This creates a normalized spectrogram or NS, in which each frequency band from the signal has substantially the same weight. In the embodiment, each 30 second epoch is represented by a "preferred frequency" which is the frequency with the largest z score within that epoch.

This creates a special frequency space called the Preferred Frequency space. Analysis of how those patterns are formed and analysis of the characteristics of the patterns can be done. Different brain states, therefore, can be defined according to a discrimination function, where the discrimination function looks for certain activity in certain areas, and non-activity in other areas. The function may evaluate brain states according to which of the frequency at areas have activity and which do not have activity.

More generally, however, any form of dynamic spectral scoring can be carried out on the compensated data. The discrimination function may require specific values, or may simply require a certain amount of activity to be present or not present, in each of a plurality of frequency ranges. The discrimination function may simply match envelopes of frequency response. The discrimination function may also look at spectral fragmentation and temporal fragmentation.

A second normalization which is carried out across frequencies. The second normalization produces a doubly normalized spectrogram. This produces a new frequency space, in which the bands become even more apparent. The doubly normalized spectrogram values can be used to form filters that maximally separate the values within the space.

A clustering technique which is carried out on the doubly normalized frequency. For example, the clustering technique may be a K means technique as described in the previous embodiments. Each cluster can represent an intention state.

The clusters are actually multi dimensional clusters, which can themselves be graphed to find additional information. The number of dimensions can depend on the number of clustering variables. This illustrates how the doubly normalized spectrogram also allows many more measurement characteristics.

Measurement of the average spread in normalized power across frequency which illustrates the spectral fragmentation is also possible. Fragmentation values can alternatively be based on temporal fragmentation for the different states may also be used as part of the discrimination function.

These two functions are evaluated on the doubly normalized spectrum, relying on homogeneous increases in gain at all frequencies as caused movement artifacts and would lead to abnormally elevated fragmentation values in the singly normalized spectrum. These fragmentation values may be used as part of the discrimination function. Importantly, and as described above, this discrimination function is typically not apparent from any previous analysis technique, including manual techniques.

The computation may be characterized by segmenting, or may use overlapping windows or a sliding window, to increase the temporal registration. This enables many techniques that have never been possible before. By characterizing on-the-fly, this enables distinguishing using the dynamic spectral scoring, between relaxation states and intention states using the brainwave signature alone.

The exemplary methods for data analysis described above were combined with a standard non-invasive EEG method for humans. The result is the ability to non-invasively extract attenuated rhythms in animals, automatically analyze the brain activity from a single channel of EEG, and sufficiently classify the brain state parameters for the animals.

EXAMPLE 1

Single-Channel iBrain EEG recordings were conducted in a high-functioning 70 year old ALS patient attempting to move one of four limbs after a verbal cue: the left and right hand and foot. Raw EEG signals were analyzed with the SPEARS algorithm in part to make high-frequency/low spectral power signals detectable. Concurrent video recordings were obtained. During the attempted movements, the subject's brain activity demonstrated distinct broad-spectrum pulses extending to the Gamma and ultra-high Gamma ranges. Such pulses were present in the absence of actual movement and absent when the subject was not attempting motion. Activity in the Alpha range was detected when the subject closed his eyes, as expected. The use of such high bandwidth biomarkers based on intended movements to a library of words will allow the conversion of the signals into speech, thus providing ALS sufferers with communication tools more dependent on the brain than on the body.

Specifically, application of the methods of the present invention reveals high frequency patterns matching the timing of a subject's actual, imagined, or intended movements. In an example application, the frequency spectrum is generated from the time series data and normalized to reveal these higher frequencies which a standard method does not reveal. An application of this to brain EEG data is shown in FIG. 1. In this example, a high-functioning 70-year-old subject, who is an ALS patient and immobile, was asked to close the eyes, rest, or imaging a hand or foot. For each of these tasks, the subject was given a verbal cue to begin the task and another cue after four seconds to stop. Six seconds later the task was repeated, for a total of 12 attempts per task and 120 seconds of time. FIG. 1 shows the standard frequency power spectrum in (i) and the enhanced frequency power spectrum in (ii) of the ALS subject while performing these tasks. The stronger signals appear redder while the weaker signals decrease in intensity through orange, yellow, and blue shades. Clear bands of high frequency activity which approximate the timing of the cues to begin and end the task appear with high intensity in the enhanced spectrum. FIG. 1 A presents this for the task of closing eyes for four seconds. FIG. 1 B presents this for the task of imagining or attempting to squeeze the left hand for four seconds and relax for six seconds. FIGS. 1 C, D, and E show the same, but for the tasks of imagining or attempting to squeeze the right hand, left foot, and right foot, respectively. In all cases, the spectrogram generated in this application clearly reveals the high frequency spectral content approximating the timing of the attempt by the subject to perform the indicated task. FIG. 1 F presents the same spectral analyses for the same subject, but at rest, and displays a very different timing of high frequency content, which may represent ambient noise, background talk, and/or baseline electrical activity.

EXAMPLE 2

Figure 2:
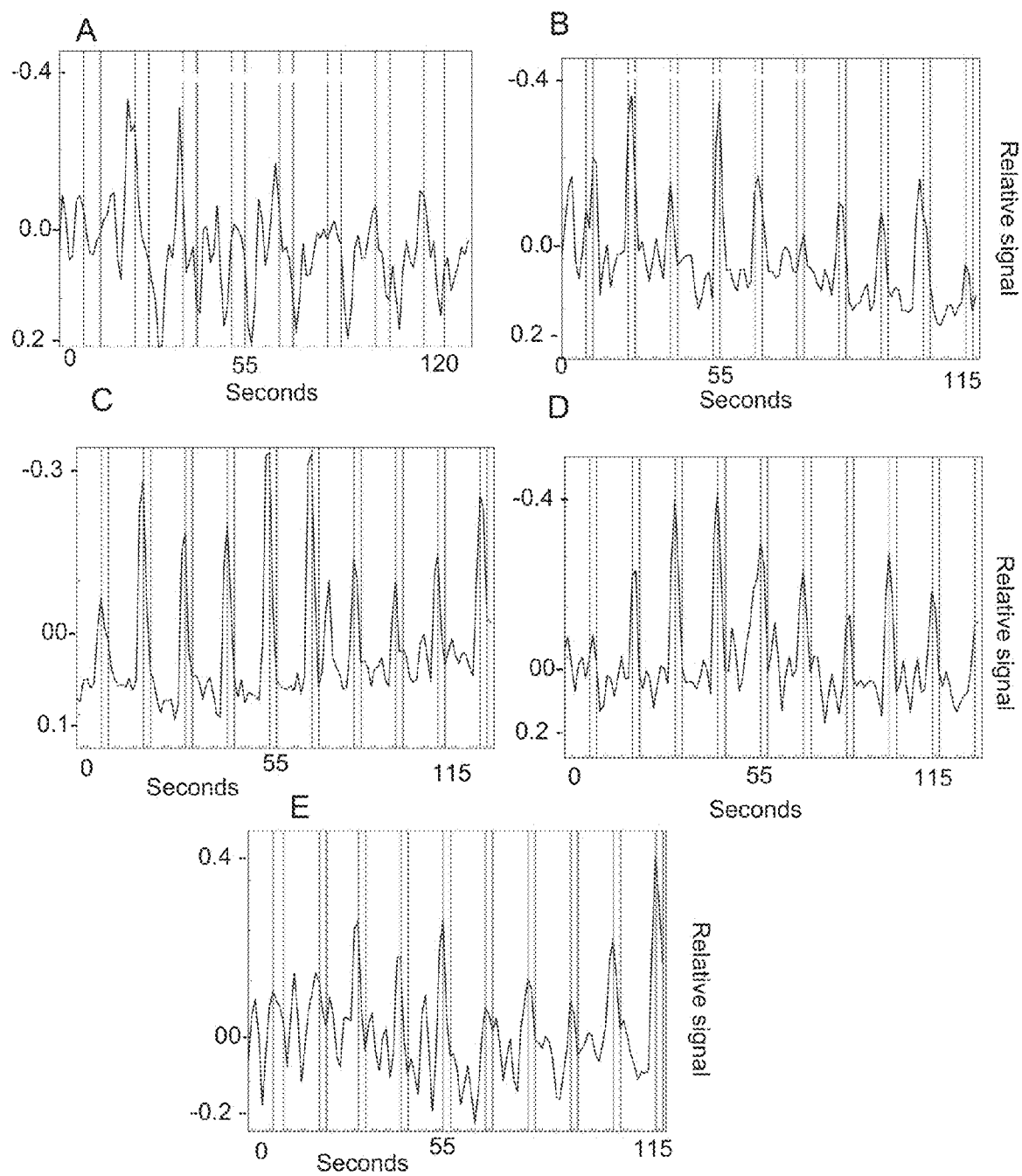
FIG. 2, A-E are data for the same tasks as indicated in FIGS. 1 A-E analyzed by the methods of the present invention (absent the resting state of FIG. 1 F). The green lines indicate the timing of the verbal cue to start the two- or four-second task, and red lines indicate the time of the verbal cue to stop the task and relax for ten seconds.

Application of the methods of the present invention in the ALS patient described in Example 1 reveals components of the data which approximate time of events. FIG. 2 presents one such application of the methods of the present invention (here with single channel component analysis on the doubly normalized spectrogram) to reveal uncorrelated independent data components. FIGS. 2 A-E are data from the same tasks as indicated in FIGS. 1 A-E. Each plot shows the resulting extracted independent component, after the full analysis as described, having peaks approximating the individual tasks attempted by the subject. The green lines indicate the timing of the verbal cue to start the four-second task, and red lines indicate the time of the verbal cue to stop the task and relax for six seconds. Peaks in each component generally align with the start of the task being performed (indicated by peak points at, on, or just after the green lines). This analysis can also be combined with that in Example 1 to strengthen or corroborate event detection and timing.

EXAMPLE 3

Figure 3:
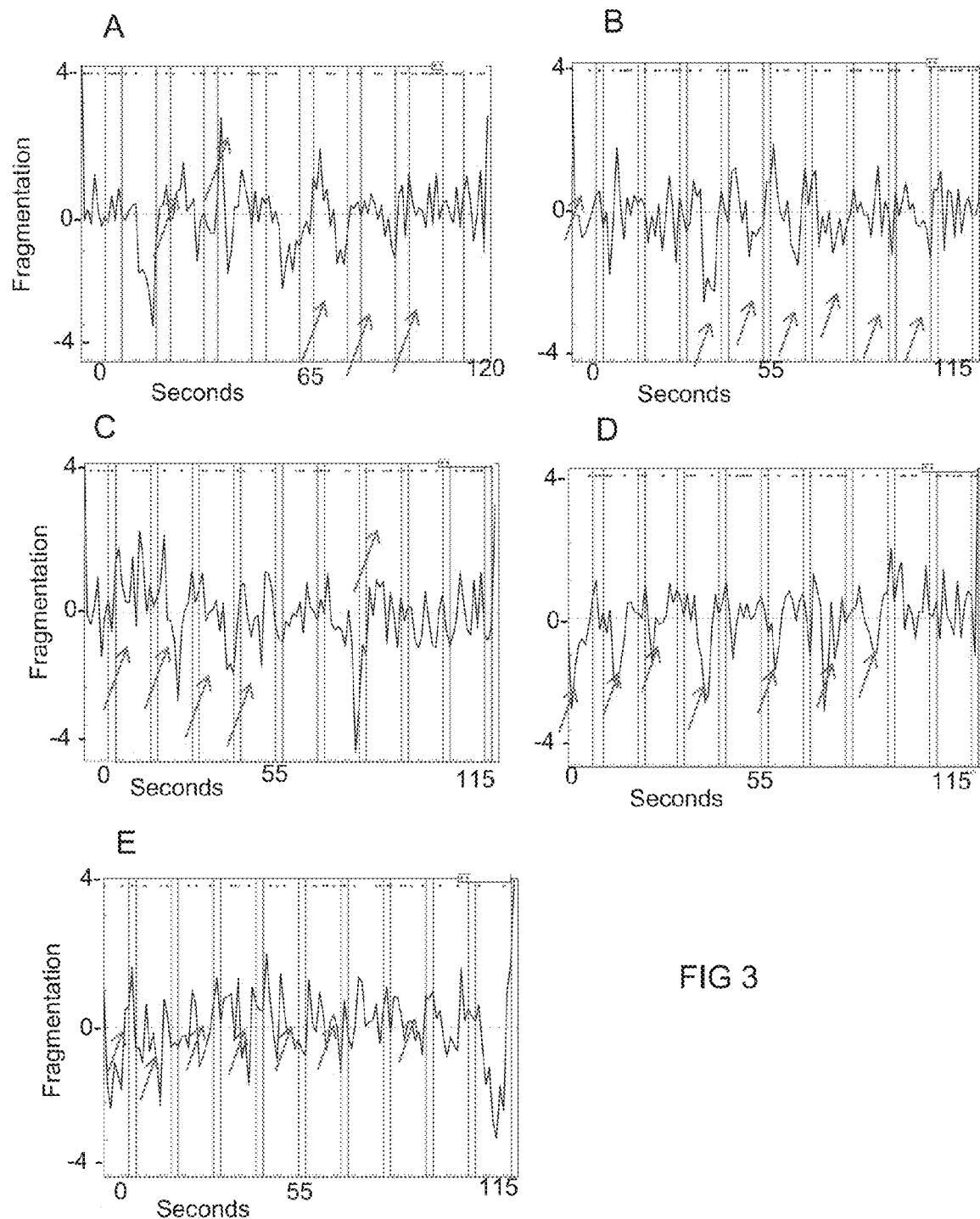
FIG. 3, A-E are data for the same tasks as indicated in FIGS. 1 A-E analyzed using temporal fragmentation with the methods of the present invention (absent the resting state of FIG. 1 F). The green lines indicate the timing of the verbal cue to start the two- or four-second task, and red lines indicate the time of the verbal cue to stop the task and relax for ten seconds.

Application of the methods of the present invention in the ALS patient described in Example 1 to single channel brain EEG data to assess data stability and reveal changes in data stability which represent intended actions are provided. Specifically, application of the methods of the present invention to generate temporal fragmentation reveals changes in stability which approximate the timing and duration of intended actions. FIGS. 3 A-E present the temporal fragmentation of the same tasks as indicated in FIGS. 1 A-E. In each plot, the shift in points from negative to positive represents a decrease in stability. These shifts approximate both the verbal cue to start the task (green lines) as the stability starts to decrease and the positive shift begins, and the verbal cue to end the task (red lines) as the data begin to stabilize end the positive shift ends. Zero-line crossings (purple dots) increase for unstable periods (during or just after the task) and decrease in count for stable periods (relaxation period before or after each task). These shifts and line crossings can also be combined with methods in Examples 1 to strengthen or corroborate event detection and timing.

EXAMPLE 4

Figure 4:
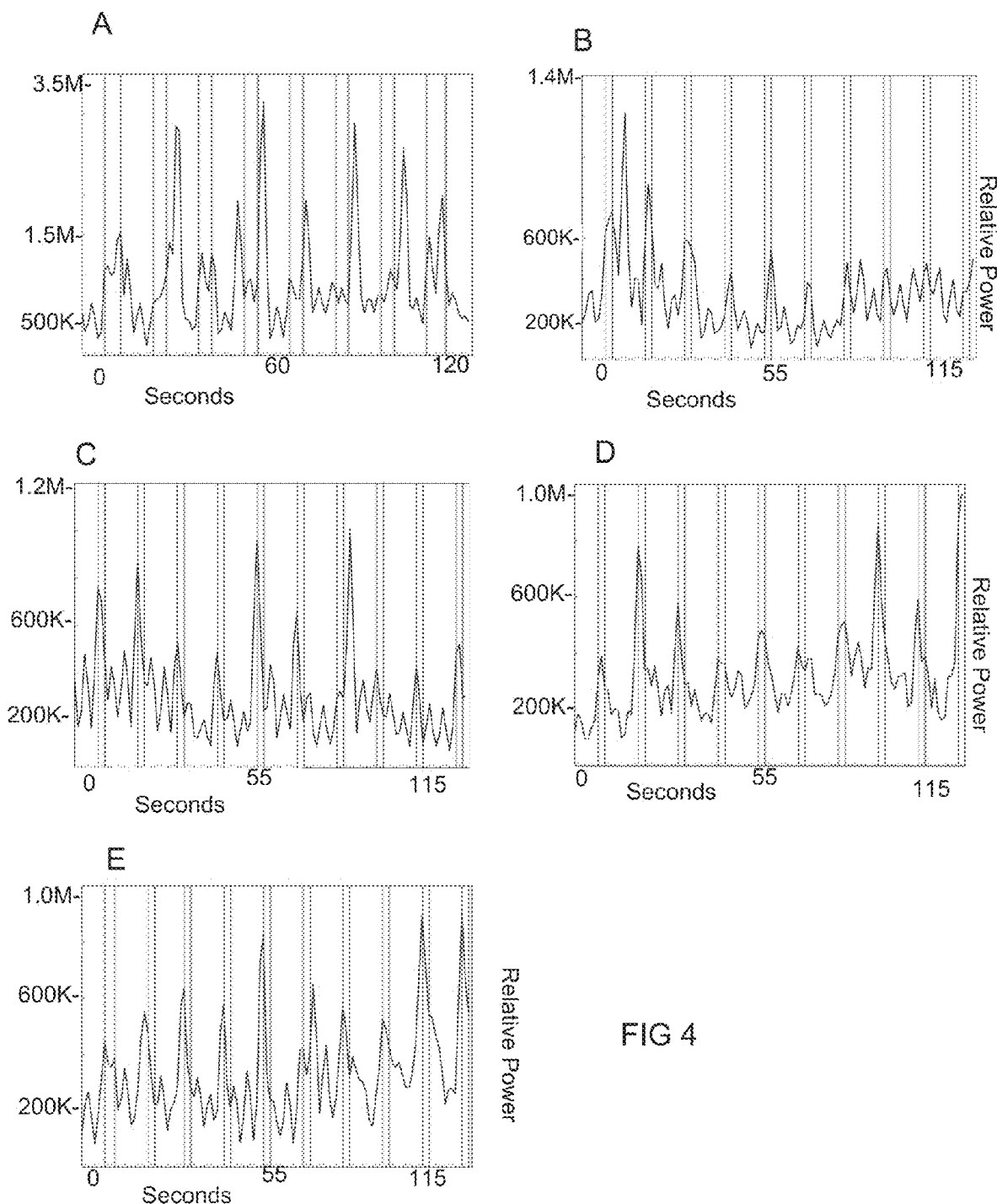
FIG. 4, A-E are data for the same tasks as indicated in FIGS. 1 A-E analyzed using one or more normalizations (absent the resting state of FIG. 1 F). Specifically, the graphs plot summed high frequency power in the gamma and ultra high gamma (hgamma) range. The green lines indicate the timing of the verbal cue to start the two- or four-second task, and red lines indicate the time of the verbal cue to stop the task and relax for ten seconds.
Figure 5:
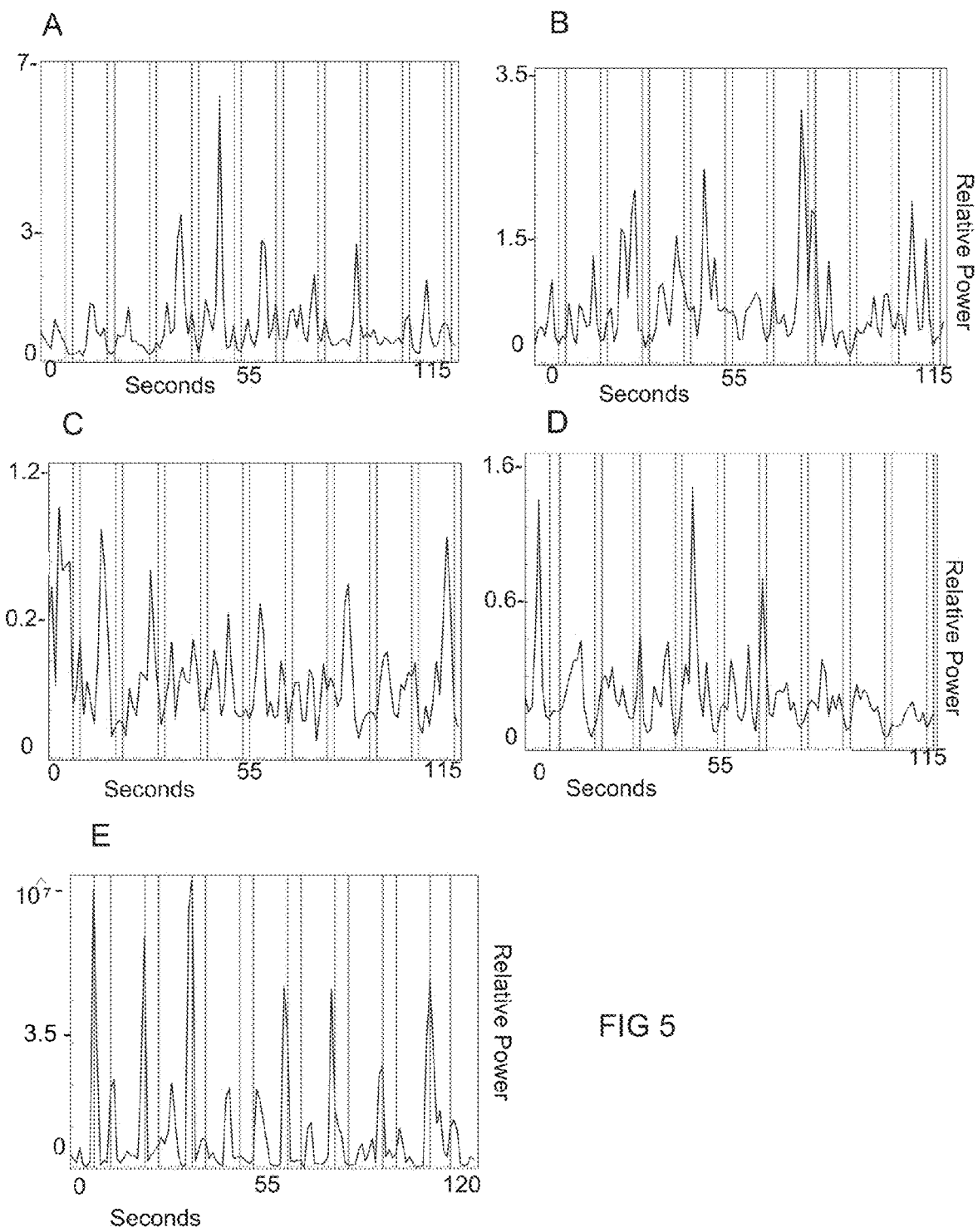
FIG. 5, A-E are data for the same tasks as indicated in FIGS. 1 A-E analyzed using one or more normalizations (absent the resting state of FIG. 1 F). Specifically, the graphs plot summed alpha frequency power to the summed gamma frequency power for 5 A-D, while delta frequency was utilized for 5 F (closed eyes). The green lines indicate the timing of the verbal cue to start the two- or four-second task, and red lines indicate the time of the verbal cue to stop the task and relax for ten seconds.

Detection of high frequency events correlated with low frequency events and event timing in the ALS patient of Example 1. Generation of the spectrogram followed by one or more normalizations across one or both data axes, followed by feature sharpening using the doubly normalized spectrogram, followed by extraction of standard known frequencies, frequency ranges, their sums, their ratios, and/or other frequency relationships, reveals event timing, spacing, and/or duration. FIGS. 4 A-E present tasks as in FIGS. 1 A-B, plotting summed high frequency power in the gamma and ultra high gamma (hgamma) range of frequencies (all those >30 Hz). In brain EEG, increased power in these frequencies correlate with heightened concentration such as occurs when imagining moving a limb. Peaks in the high frequency power summations approximate the timing of the task, indicated by the columns of green (task start) and red (task end) lines. FIGS. 5 A-D present tasks as in FIG. 1, for squeezing right hand, left hand, right foot, and left foot, respectively, plotting the ratio of the summed alpha frequency (8-13 Hz) power to the summed gamma frequency power (30-50 Hz). Increase power in the alpha frequencies in brain EEG correlates with relaxation of mental effort such as after a length of time attempting to squeeze a limb. Thus, alpha and gamma frequency power are inversely related for these tasks and peaks in the alpha-to-gamma ratio appear in between tasks (between red line indicating stop and green line indicating start again). FIG. 5 E shows the analysis of the delta frequency (<5 Hz) during the close eyes task. Delta frequency power correlates with changes in eye open or closed state and approximate the timing of the subject closing (green lines) and opening (red lines) eyes. These and other frequency analyses can be combined with each other and the methods in Examples 1, 2, and 3 to strengthen or corroborate event detection and timing, as well as to characterize the event with the known related brain state implied by the frequencies analyzed.

EXAMPLE 5

Figure 8:
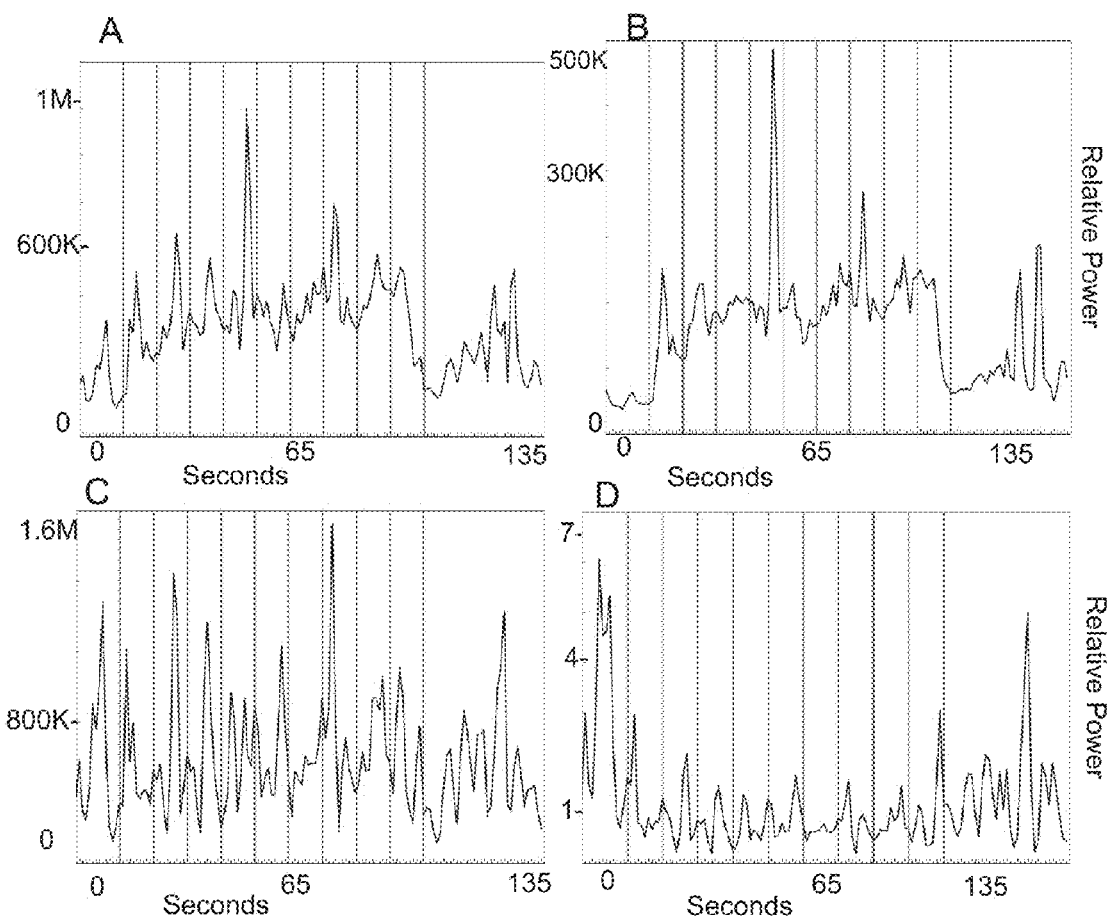
FIG. 8, data are analyzed using one or more normalizations and visualizing and alternating between kicking a football and viewing a bedroom on gamma frequency power (A), alpha frequency power (B), summed alpha and gamma frequency power (C), and the ratio of summed alpha and ultra high gamma frequency power. The green lines indicate the timing of the verbal cue to start, and red lines indicate the time of the verbal cue to stop ten second intervals.

Simultaneous detection of multiple events co-occurring in time for a second ALS patient. Generation of the spectrogram followed by one or more normalizations across one or both data axes, followed by feature sharpening, followed by extraction of standard known frequencies, frequency ranges, their sums, their ratios, and/or other frequency relationships, reveals multiple events in one analysis. FIG. 8 shows data from a task designed to elicit both an increase in concentration (increase gamma frequency power) and shifts in thought which would display as reduced and increased relaxation (changes in alpha frequency power). An immobile ALS patient subject was instructed to alternate between two 10-second imaginings (kicking a football, green lines, and viewing the bedroom, red lines), repeating 5 times. FIG. 8 A plots the normalized and enhanced gamma frequency power, displaying a sharp increase at the start of the alternation sequence (first green line, at 13 seconds) and subsequent decrease at the end of the full sequence (last red line, at 103 seconds). FIG. 8 B plots the normalized and enhanced alpha frequency power, showing changes in relaxation states between the two different imaginings (peaks between colored lines). FIG. 8 C plots the normalized and enhanced alpha and gamma power, showing the simultaneous detection of both the plateau of gamma frequency power during the set of imaginings, and the alpha peaks when changing imaginings, as two unique signals detected in one analysis. FIG. 8 D plots the ratio of the normalized and enhanced alpha to ultra high gamma (hgamma), with a drop in the ratio at the beginning of the sequence, the individual peaks at each imagining, and a rise in the ratio after the sequence.

EXAMPLE 6

Figure 10:
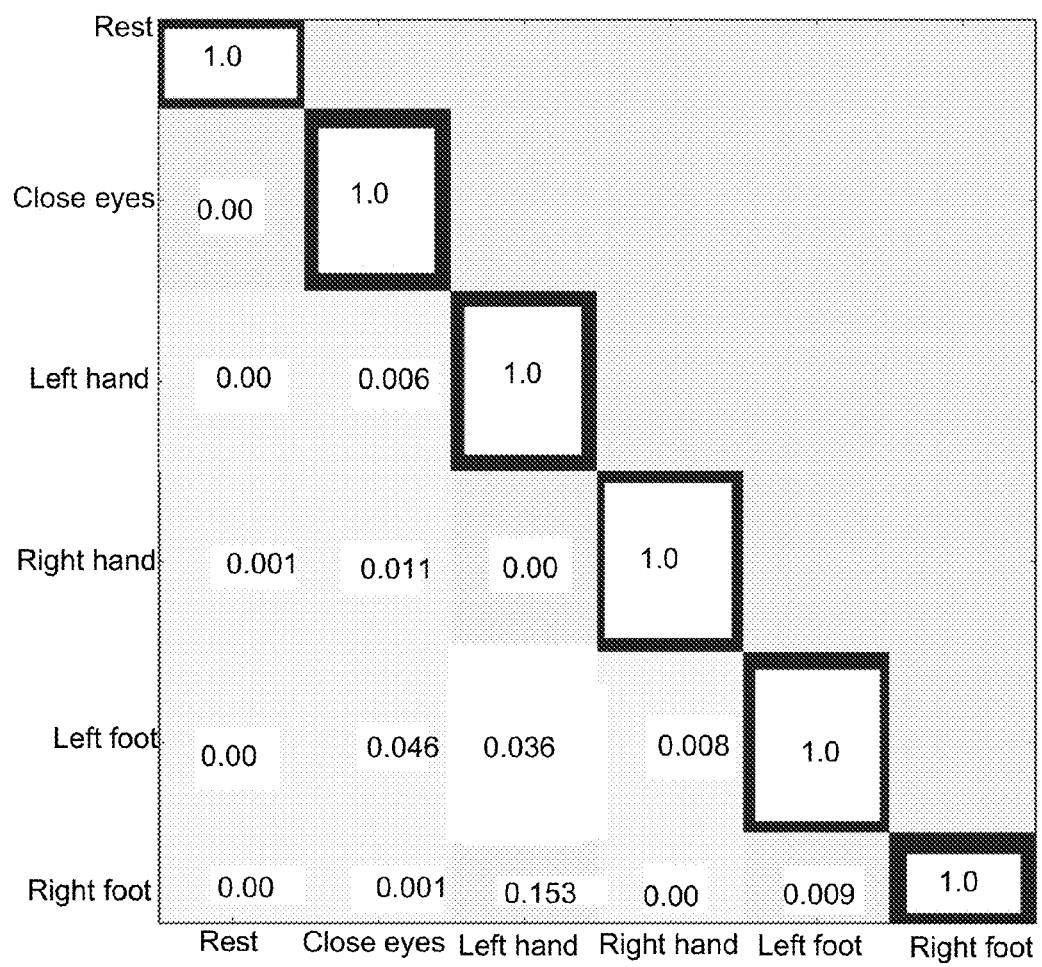
FIG. 10 is a Kolmogorov-Smirnov (KS) two-sample test with 10-fold, cross-axes normalized iterative preferred frequency spectrogram from each task as listed in FIGS. 1 A-E performed by an immobile ALS subject indicates that more than a single intended event can be identified. Each spectrogram is from a distribution different from that of any other task (and to no lesser extent in this particular trial left hand squeezing from right foot squeezing in this subject).

Use of the iteratively normalized spectrogram to differentiate and characterize more than one type of intended events. Analysis including application of the SPEARS algorithm followed by a Klomogorov-Smirnov (KS) two-sample test for same-distribution sampling between any two spectrograms reveals distinguishable imagined motor movements. This application enables multiple degrees of freedom based on at least one event type being differentiable from others. KS test p values of the 10-fold, cross-axes normalized spectrogram from each task as listed in FIGS. 1 A-E performed by an immobile ALS subject indicate that each spectrogram is from a distribution different from rest (P<0.01) (Table 1) and from that of almost any other task (P<0.05) (FIG. 10), and to a lesser extent in the left hand and right foot in this particular trial, becoming an effective application for characterizing the same or multiple events at detection.

TABLE 1

KS Test p values of imagined tasks against Rest

| Task | Klomogorov-Smirnov p Value Compared to Rest |
|---|---|
| Rest | 1.00 |
| Close Eyes | <0.001 ($1.18 \times 10^{-6}$) |
| Squeeze Left Hand | <0.001 ($3.15 \times 10^{-17}$) |
| Squeeze Right Hand | <0.001 ($6.81 \times 10^{-4}$) |
| Squeeze Left Foot | <0.001 ($8.32 \times 10^{-9}$) |
| Squeeze Right Foot | <0.001 ($1.64 \times 10^{-16}$) |

Throughout this application, various publications, patents, and/or patent applications are referenced in order to more fully describe the state of the art to which this invention pertains. The disclosures of these publications, patents, and/or patent applications are herein incorporated by reference in their entireties, and for the subject matter for which they are specifically referenced in the same or a prior sentence, to the same extent as if each independent publication, patent, and/or patent application was specifically and individually indicated to be incorporated by reference.

Although only a few embodiments have been disclosed in detail above, other embodiments are possible and the inventors intend these to be encompassed within this specification. The specification describes specific examples to accomplish a more general goal that may be accomplished in another way. This disclosure is intended to be exemplary, and the claims are intended to cover any modification or alternative which might be predictable to a person having ordinary skill in the art. For example, other applications are possible, and other forms of discrimination functions and characterization is possible. While the above extensively described characterizing the frequency in terms of its "preferred frequency", it should be understood that more rigorous characterization of the information may be possible. Also, while the above only refers to determining intention states from the EEG data, and refers to only a few different kinds of determination of intention states, it should be understood that other applications are contemplated.

Having illustrated and described the principles of the invention in exemplary embodiments, it should be apparent to those skilled in the art that the described examples are illustrative embodiments and can be modified in arrangement and detail without departing from such principles. Techniques from any of the examples can be incorporated into one or more of any of the other examples. It is intended that the specification and examples be considered as exemplary only, with a true scope and spirit of the invention being indicated by the following claims.

What is claimed:

1. A method to detect an intentional brain signal from a subject comprising:
   (a) attaching at least a single sensor to the subject;
   (b) obtaining data indicative of brain activity;
   (c) analyzing said data indicative of brain activity, wherein analyzing comprises computing a spectrogram of the data, normalizing the spectrogram of the data at least once, time over frequency, and normalizing the spectrogram of the data at least once, frequency over time; and
   (d) correlating said analyzed data to an intentional higher cognitive function from the subject.

2. The method according to claim 1, wherein said obtaining data is received non-invasively by applying at least the single sensor to the subject.

3. The method according to claim 2, wherein said at least a single sensor is selected from the group consisting of a single dry sensor or a single wet sensor.

4. The method according to claim 2, wherein said obtaining data is received from at least a single channel of EEG, EMG, EOG, MEG, ECoG, iEEG, fMRI, LFP, or a peripheral channel modulated by an intention of the subject.

5. The method according to claim 4, wherein said obtaining data is received from at least a single channel of EEG.

6. The method according to claim 5, wherein said obtaining data is received from a multi channel detector comprising at least a single channel EEG, EMG, EOG, MEG, ECoG, iEEG, fMRI, LFP or a peripheral channel modulated by the subject's intention.

7. The method according to claim 2, wherein said obtaining data is received wirelessly.

8. The method according to claim 1, wherein the analyzing further comprises performing a principal and/or independent component analysis of the normalized spectrogram.

9. The method according to claim 1, wherein said analyzing comprises performing a temporal fragmentation analysis.

10. The method according to claim 1, wherein said analyzing comprises performing a preferred frequency analysis.

11. The method according to claim 10, wherein the preferred frequency analysis is performed on the spectrogram that has been normalized at least two times.

12. The method according to claim 1, wherein said analyzing comprises performing a spectral fragmentation analysis.

13. The method according to claim 1, further comprising after the correlating, translating the analyzed data to effect a task associated with the higher cognitive function.

14. The method according to claim 13, wherein the task is selected from the group consisting of simulating speech on a display, simulating speech with a voice synthesizer and movement of an artificial prosthesis.

15. The method according to claim 13, wherein the higher cognitive function is selected from the group consisting of intent, speech, memory recall, planned motion, thought and imagination.

16. A method to detect a brain signal from a subject correlated with at least one unintended event comprising:
   (a) attaching at least a single sensor to the subject;
   (b) obtaining data indicative of brainwave activity;
   (c) analyzing said data indicative of brain activity, wherein analyzing comprises computing a spectrogram of the data, normalizing the spectrogram of the data at least once, time over frequency, and normalizing the spectrogram of the data at least once, frequency over time; and (d) correlating said analyzed data to at least one unintended event.

17. The method according to claim 16, further comprising, after the correlating, triggering an alarm.

18. The method according to claim 16, further comprising, after the correlating, responding to the unintended event to ameliorate its effect.

19. The method according to claim 18, wherein the response to the unintended event comprises intervening to alter, suppress or prepare for the unintended event.

20. The method according to claim 16, wherein the unintended event is selected from the group consisting of a high fragmentation event, a change in fragmentation of an event, a surprise, a tremor, a spasm, an injury, an epileptic seizure, a migraine, a stroke, a heart attack and an infarction.

21. The method according to claim 16, wherein said analyzing comprises performing a temporal fragmentation analysis.

22. The method according to claim 16, wherein said analyzing comprises performing a preferred frequency analysis.

23. The method according to claim 22, wherein the preferred frequency analysis is performed on the spectrogram that has been normalized at least two times.

24. The method according to claim 16, wherein said analyzing comprises performing a spectral fragmentation analysis.

25. The method according to claim 16, wherein the analyzing further comprises
performing a principal and/or independent component analysis of the normalized spectrogram.

26. A method to detect an intentional signal from a subject comprising:
(a) attaching at least one detector capable of detecting the intentional signal to the subject;
(b) obtaining data indicative of detected activity using EEG, EMG, EOG, MEG, ECG, ECoG, iEEG, LFP, fMRI or a peripheral channel modulated by an intention of the subject;
(c) analyzing said data indicative of the detected activity, wherein analyzing comprises computing a spectrogram of the data, normalizing the spectrogram of the data at least once, time over frequency, and normalizing the spectrogram of the data at least once, frequency over time; and
(d) correlating said analyzed data to an intentional higher cognitive function from the subject.

* * * * *